(12) United States Patent
Berthon-Jones et al.

(10) Patent No.: US 6,367,474 B1
(45) Date of Patent: Apr. 9, 2002

(54) ADMINISTRATION OF CPAP TREATMENT PRESSURE IN PRESENCE OF APNEA

(75) Inventors: Michael Berthon-Jones, Leonay; Steven Paul Farrugia, Peakhurst, both of (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/008,743

(22) Filed: Jan. 19, 1998

(30) Foreign Application Priority Data

Nov. 7, 1997 (AU) .............................................. PP0269

(51) Int. Cl.⁷ .............................................. A61M 16/00
(52) U.S. Cl. .............................. 128/204.23; 128/204.18; 128/204.21; 128/204.26
(58) Field of Search ....................... 128/204.21, 204.23, 128/204.26, 204.18

(56) References Cited

U.S. PATENT DOCUMENTS

| | | | |
|---|---|---|---|
| 2,904,033 A | | 9/1959 | Shane |
| 3,559,638 A | | 2/1971 | Potter |
| 3,595,228 A | | 7/1971 | Simon et al. |
| 3,611,801 A | | 10/1971 | Paine et al. |
| 3,802,417 A | | 4/1974 | Lang |
| 3,817,246 A | * | 6/1974 | Weigl |
| 3,882,847 A | | 5/1975 | Jacobs |
| 3,903,875 A | * | 9/1975 | Hughes |
| 3,914,994 A | | 10/1975 | Banner |
| 3,932,054 A | * | 1/1976 | McKelvey |
| 3,985,467 A | * | 10/1976 | Lefferson |
| 3,989,037 A | | 11/1976 | Franetzki |
| 4,006,634 A | | 2/1977 | Billette et al. |
| 4,083,245 A | | 4/1978 | Osborn |
| 4,312,235 A | | 1/1982 | Daigle |
| 4,320,766 A | | 3/1982 | Alihanka et al. |
| 4,322,594 A | | 3/1982 | Brisson |
| 4,381,788 A | | 5/1983 | Douglas |
| 4,387,722 A | * | 6/1983 | Kearns |
| 4,414,982 A | | 11/1983 | Durkan |

(List continued on next page.)

FOREIGN PATENT DOCUMENTS

| | | |
|---|---|---|
| AU | B-59270/90 | 12/1990 |
| AU | A-62221/90 | 3/1991 |
| AU | A-76019/91 | 1/1992 |
| AU | A-33877/93 | 4/1993 |
| AU | A-48747/93 | 12/1993 |
| AU | A-34471/95 | 2/1996 |
| AU | A-40711-95 | 4/1996 |
| EP | 0 425 092 A1 | 9/1989 |
| EP | 0 452 001 A2 | 3/1990 |
| EP | 0 461 281 A1 | 12/1991 |
| EP | 0651971 A1 | 5/1995 |
| EP | 0 656 216 A2 | 6/1995 |
| EP | 0 714 670 A2 | 6/1996 |
| EP | 0 765 631 A2 | 4/1997 |

(List continued on next page.)

*Primary Examiner*—John G. Weiss
*Assistant Examiner*—Metal Patel
(74) *Attorney, Agent, or Firm*—Gottlieb, Rackman & Reisman, P.C.

(57) ABSTRACT

CPAP treatment apparatus having a controllable flow generator operable to produce breathable gas at a treatment pressure elevated above atmosphere to a patient by a delivery tube coupled to a mask having a connection with a patient's airway. A sensor generates a signal representative of patient respiratory flow that is provided to a controller. The controller is operable to determine the occurrence of an apnea from a reduction in respiratory airflow below a threshold, and if an apnea has occurred, to determine the duration of the apnea and to cause the flow generator to increase the treatment pressure by an amount which is an increasing function of the duration of the apnea, and a decreasing function of the treatment pressure immediately before the apnea.

40 Claims, 4 Drawing Sheets

U.S. PATENT DOCUMENTS

| | | | |
|---|---|---|---|
| 4,433,693 A | | 2/1984 | Hochstein |
| 4,448,058 A | * | 5/1984 | Jaffe et al. |
| 4,499,914 A | * | 2/1985 | Schebler |
| 4,506,666 A | | 3/1985 | Durkan |
| 4,550,615 A | | 11/1985 | Grant |
| 4,550,726 A | | 11/1985 | McEwen |
| 4,558,710 A | | 12/1985 | Eichler |
| 4,570,631 A | | 2/1986 | Durkan |
| 4,576,179 A | | 3/1986 | Manus et al. |
| 4,580,575 A | | 4/1986 | Birnbaum et al. |
| 4,595,016 A | | 6/1986 | Fertig et al. |
| 4,602,644 A | | 7/1986 | DiBenedetto et al. |
| 4,630,614 A | * | 12/1986 | Atlas |
| 4,648,396 A | | 3/1987 | Raemer |
| 4,648,407 A | | 3/1987 | Sackner |
| 4,677,975 A | | 7/1987 | Edgar et al. |
| 4,686,974 A | | 8/1987 | Sato et al. |
| 4,686,999 A | * | 8/1987 | Snyder et al. |
| 4,738,266 A | | 4/1988 | Thatcher |
| 4,777,963 A | | 10/1988 | McKenna |
| 4,795,314 A | * | 1/1989 | Prybella et al. |
| 4,802,485 A | | 2/1989 | Bowers et al. |
| 4,803,471 A | | 2/1989 | Rowland |
| 4,819,629 A | | 4/1989 | Jonson |
| 4,823,788 A | * | 4/1989 | Smith et al. |
| 4,825,802 A | | 5/1989 | Le Bec |
| 4,827,922 A | * | 5/1989 | Champain et al. |
| 4,838,258 A | | 6/1989 | Dryden et al. |
| 4,844,085 A | | 7/1989 | Gattinoni |
| 4,860,766 A | | 8/1989 | Sackner |
| 4,870,960 A | * | 10/1989 | Hradek |
| 4,887,607 A | | 12/1989 | Beatty |
| 4,915,103 A | * | 4/1990 | Visveshwara et al. |
| 4,938,210 A | | 7/1990 | Shene |
| 4,938,212 A | | 7/1990 | Gnook et al. |
| 4,957,107 A | * | 9/1990 | Sipin |
| 4,960,118 A | | 10/1990 | Pennock |
| 4,971,065 A | | 11/1990 | Pearce |
| 4,972,842 A | | 11/1990 | Korten et al. |
| 4,982,738 A | | 1/1991 | Griebel |
| 4,986,269 A | | 1/1991 | Hakkinen |
| 4,989,599 A | | 2/1991 | Carter |
| 5,024,219 A | | 6/1991 | Dietz |
| 5,052,400 A | | 10/1991 | Dietz |
| 5,063,922 A | | 11/1991 | Hakkinen |
| 5,069,222 A | | 12/1991 | McDonald, Jr. |
| 5,090,248 A | | 2/1992 | Cimmino et al. |
| 5,105,354 A | * | 4/1992 | Nishimura |
| 5,134,995 A | * | 8/1992 | Gruenke et al. |
| 5,161,541 A | | 11/1992 | Bowman et al. |
| 5,170,798 A | | 12/1992 | Riker |
| 5,174,287 A | | 12/1992 | Kallok et al. |
| 5,178,138 A | | 1/1993 | Walstrom et al. |
| 5,190,048 A | | 3/1993 | Wilkinson |
| 5,195,528 A | | 3/1993 | Hok |
| 5,199,424 A | | 4/1993 | Sullilvan et al. |
| 5,203,343 A | | 4/1993 | Axe et al. |
| 5,231,983 A | | 8/1993 | Matson et al. |
| 5,233,983 A | | 8/1993 | Markowitz et al. |
| 5,239,995 A | | 8/1993 | Estes et al. |
| 5,245,995 A | | 9/1993 | Sullivan et al. |
| 5,259,373 A | | 11/1993 | Gruenke et al. |
| 5,280,784 A | | 1/1994 | Kohler |
| 5,293,864 A | * | 3/1994 | McFadden |
| 5,295,491 A | | 3/1994 | Gevins |
| 5,303,700 A | | 4/1994 | Weismann et al. |
| 5,311,875 A | | 5/1994 | Stasz |
| 5,313,937 A | | 5/1994 | Zdrojkowski |
| 5,322,057 A | | 6/1994 | Raabe et al. |
| 5,327,899 A | | 7/1994 | Harris et al. |
| 5,335,654 A | | 8/1994 | Rapoport |
| 5,353,788 A | | 10/1994 | Miles |
| 5,360,008 A | | 11/1994 | Campbell, Jr. |
| 5,388,571 A | | 2/1995 | Roberts et al. |
| 5,394,882 A | | 3/1995 | Mawhinney |
| 5,404,871 A | | 4/1995 | Goodman et al. |
| 5,413,111 A | | 5/1995 | Wilkinson |
| 5,433,193 A | | 7/1995 | Sanders et al. |
| 5,438,980 A | * | 8/1995 | Phillips |
| 5,443,075 A | * | 8/1995 | Holscher |
| 5,448,996 A | * | 9/1995 | Bellin et al. |
| 5,458,137 A | | 10/1995 | Axe et al. |
| 5,479,920 A | | 1/1996 | Piper et al. |
| 5,479,939 A | | 1/1996 | Ogino |
| 5,483,969 A | | 1/1996 | Testerman et al. |
| 5,490,502 A | | 2/1996 | Rapoport et al. |
| 5,503,146 A | | 4/1996 | Froehlich et al. |
| 5,507,282 A | | 4/1996 | Younes |
| 5,509,404 A | | 4/1996 | Lloyd et al. |
| 5,513,631 A | | 5/1996 | McWilliams |
| RE35,295 E | | 7/1996 | Estes et al. |
| 5,535,738 A | | 7/1996 | Estes et al. |
| 5,535,739 A | | 7/1996 | Rapoport et al. |
| 5,537,997 A | * | 7/1996 | Mechlenberg et al. . 128/204.23 |
| 5,540,219 A | | 7/1996 | Mechlenburg et al. |
| 5,540,220 A | * | 7/1996 | Gropper |
| 5,540,733 A | | 7/1996 | Testerman et al. |
| 5,546,933 A | | 8/1996 | Rapoport et al. |
| 5,546,952 A | | 8/1996 | Erickson |
| 5,549,106 A | * | 8/1996 | Gruenke et al. |
| 5,549,655 A | | 8/1996 | Erickson |
| 5,551,419 A | | 9/1996 | Froehlich et al. |
| 5,558,099 A | | 9/1996 | Bowman et al. |
| 5,570,682 A | * | 11/1996 | Johnson |
| 5,588,439 A | | 12/1996 | Hollub |
| 5,598,838 A | | 2/1997 | Servidio et al. |
| 5,605,151 A | | 2/1997 | Lynn |
| 5,608,647 A | | 3/1997 | Rubsamen et al. |
| 5,630,411 A | * | 5/1997 | Holscher |
| 5,642,730 A | | 7/1997 | Baran |
| 5,647,351 A | | 7/1997 | Weismann et al. |
| 5,655,520 A | | 8/1997 | Howe et al. |
| 5,660,171 A | * | 8/1997 | Kimm et al. |
| 5,666,946 A | | 9/1997 | Langenback |
| 5,701,883 A | | 12/1997 | Hete et al. |
| 5,704,345 A | * | 1/1998 | Berthon-Jones ........ 128/204.23 |
| 5,730,121 A | | 3/1998 | Hawkins |
| 5,740,795 A | * | 4/1998 | Brydon .................. 128/204.21 |
| 5,797,852 A | | 8/1998 | Karakasoglu et al. |
| 5,803,066 A | | 9/1998 | Rapoport et al. |
| 5,845,636 A | | 12/1998 | Gruenke et al. |
| 5,953,713 A | * | 9/1999 | Behbehani et al. ........... 706/16 |
| 5,970,975 A | * | 10/1999 | Estes et al. ............ 128/204.23 |
| 6,085,747 A | * | 7/2000 | Axe et al. ............... 128/204.23 |
| 6,135,106 A | * | 10/2000 | Dirks et al. ............ 128/204.23 |

FOREIGN PATENT DOCUMENTS

| | | |
|---|---|---|
| EP | 0 788 805 A2 | 8/1997 |
| GB | 1583273 | 1/1981 |
| GB | 2 166 871 A | 5/1986 |
| GB | 2 221 302 A | 1/1990 |
| GB | 2 294 670 A | 5/1996 |
| WO | WO 82/03548 | 10/1982 |
| WO | WO 86/05965 | 10/1986 |
| WO | WO 87/02577 | 5/1987 |
| WO | WO 89/09565 | 10/1988 |
| WO | WO 88/10108 | 12/1988 |
| WO | WO 90/14121 | 1/1990 |
| WO | WO 90/09146 | 8/1990 |
| WO | WO 91/12051 | 8/1991 |

| | | | | | | |
|---|---|---|---|---|---|---|
| WO | WO 92/11054 | 7/1992 | | WO | WO 96/32055 | 10/1996 |
| WO | WO 92/22244 | 12/1992 | | WO | WO 96/36279 | 11/1996 |
| WO | WO 93/08857 | 5/1993 | | WO | WO 96/40337 | 12/1996 |
| WO | WO 93/09834 | 5/1993 | | WO | WO 96/41571 | 12/1996 |
| WO | WO 93/21982 | 11/1993 | | WO | WO 97/05824 | 2/1997 |
| WO | WO 93/24169 | 12/1993 | | WO | WO 97/10019 | 3/1997 |
| WO | WO 94/04071 | 3/1994 | | WO | WO 97/15343 | 5/1997 |
| WO | WO 94/20018 | 9/1994 | | WO | WO 97/18752 | 5/1997 |
| WO | WO 94/22517 | 10/1994 | | WO | WO 97/20499 | 6/1997 |
| WO | WO 94/23780 | 10/1994 | | WO | WO 97/22377 | 6/1997 |
| WO | WO 95/32016 | 11/1995 | | | | |
| WO | WO 95/034917 | 12/1995 | | | | |

\* cited by examiner

ADMINISTRATION OF CPAP TREATMENT PRESSURE IN PRESENCE OF APNEA

FIELD OF THE INVENTION

This invention relates to the administration of continuous positive airway pressure (CPAP) treatment for partial or complete upper airway obstruction.

BACKGROUND OF THE INVENTION

In the Sleep Apnea syndrome a person stops breathing during sleep. Cessation of airflow for more than 10 seconds is called an "apnea". Apneas lead to decreased blood oxygenation and thus to disruption of sleep. Apneas are traditionally (but confusingly) categorized as either central, where there is no respiratory effort, or obstructive, where there is respiratory effort. With some central apneas, the airway is open, and the subject is merely not attempting to breathe. Conversely, with other central apneas and all obstructive apneas, the airway is closed. The occlusion is usually at the level of the tongue or soft palate. The airway may also be partially obstructed (i.e. narrowed or partially patent). This also leads to decreased ventilation (hypopnea), decreased blood oxygenation and disturbed sleep.

The common form of treatment of these syndromes is the administration of Continuous Positive Airway Pressure (CPAP). The procedure for administering CPAP treatment has been well documented in both the technical and patent literature. An early description can be found in U.S. Pat. No. 4,944,310 (Sullivan). Briefly stated, CPAP treatment acts as a pneumatic splint of the airway by the provision of a positive pressure, usually in the range 4–20 cm $H_2O$. The air is supplied to the airway by a motor driven blower whose outlet passes via an air delivery hose to a nose (or nose and/or mouth) mask sealingly engaged to a patient's face. An exhaust port is provided in the delivery tube proximate to the mask.

Various techniques are known for sensing and detecting abnormal breathing patterns indicative of obstructed breathing. U.S. Pat. No. 5,245,995 (Sullivan et al), for example, describes how snoring and abnormal breathing patterns can be detected by inspiration and expiration pressure measurements while sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to, ideally, subvert the occurrence of the obstructive episodes and the other forms of breathing disorder.

Automatic detection of partial upper airway obstruction and pre-emptive adjustment of nasal CPAP pressure works to prevent frank obstructive apneas in the majority of subjects with obstructive sleep apnea syndrome. However, some subjects with severe disease progress directly from a stable open upper airway to a closed airway apnea with complete airway closure, with little or no intervening period of partial obstruction. Therefore it is useful for an automatically adjusting CPAP system to also respond to a closed airway apnea by an increase in CPAP pressure. However, it is not desirable to increase CPAP pressure in response to open airway apneas, firstly because this leads to an unnecessarily high pressure, and secondly because the high pressure can reflexly cause yet further open airway apneas, leading to a vicious circle of pressure increase.

One method for distinguishing open airway apneas (requiring no increase in pressure) from closed airway apneas (requiring a pressure increase) is disclosed in European Publication No. 0 651 971 A1. During an apnea, the mask pressure is modulated at 4 Hz with an amplitude of the order of 1 cmH2O the induced airflow at 4 Hz is measured, and the conductance of the airway is calculated. A high conductance indicates an open airway. This forced oscillation method requires the ability to modulate the mask pressure at 4 Hz, which increases the cost of the device. Furthermore, the method does not work in the presence of high leak, and can falsely report that the airway is closed if the subject has a high nasal or intrapulmonary resistance.

The present invention is directed to overcoming or at least ameliorating one or more of the foregoing disadvantages in the prior art.

SUMMARY OF THE INVENTION

Therefore, the invention discloses a method for the administration of CPAP treatment pressure comprising the steps of:

supplying breathable gas to the patient's airway at an initial treatment pressure, and repeatedly:

determining a measure of respiratory airflow;

determining the occurrence of an apnea from a reduction in said measure of respiratory airflow below a threshold;

determining the duration of said apnea; and increasing the treatment pressure by an amount which is an increasing function of the duration of said apnea, and a decreasing function of the treatment pressure immediately before said apnea.

The invention further discloses CPAP treatment apparatus comprising:

a controllable flow generator operable to produce breathable gas at a pressure elevated at a pressure above atmosphere;

a gas delivery tube coupled to the flow generator;

a patient mask coupled to the tube to receive said breathable gas from the flow generator and provide said gas, at a desired treatment pressure, to the patient's airway;

a controller operable to receive input signals and to control operation of said flow generator and hence the treatment pressure; and sensor means located at the flow generator, in the delivery tube or at the mask that generates a signal input to said controller from which patient respiratory airflow is determined;

and wherein said controller is operable to determine the occurrence of an apnea from a reduction in said respiratory airflow, determine the duration of said apnea, and cause said flow generator to increase CPAP treatment pressure by an increment that is an increasing function of said apnea duration and a decreasing function of the treatment pressure immediately prior to said apnea.

In a preferred form, said sensor means can comprise a flow sensor, and said controller derives respiratory airflow therefrom.

In one preferred form said initial treatment pressure is 4 cmH2O said measure of respiratory airflow is the two second moving average RMS airflow, and said threshold is 25% of the RMS airflow over the preceding 5 minutes. In this preferred form, no increase in pressure is made for apneas of less than 10 seconds duration, or for apneas where the treatment pressure immediately prior to the apnea is more than 10 cmH2O but otherwise, the lower the treatment pressure immediately prior to the apnea, and the longer the apnea, the greater the increase in treatment pressure, up to a maximum of 8 cmH2O per minute of apnea. In this preferred form, if there is no apnea the treatment pressure is gradually reduced towards the initial minimum pressure with a time constant of 20 minutes.

The method and apparatus can advantageously be used in concert with one or more other methods for determining the occurrence of partial upper airway obstruction, such that either complete or partial upper airway obstruction can lead to an increase in pressure, but once there is no longer either complete or partial obstruction, the pressure will gradually reduce towards the initial minimum pressure.

In one particularly preferred form, partial obstruction is detected as either the presence of snoring, or the presence of characteristic changes in the shape of the inspiratory flow-vs-time curve indicative of inspiratory airflow limitation.

The method and apparatus can also advantageously be used in concert with a forced oscillation method for measuring airway patency, in which the CPAP pressure is modulated with an amplitude of, for example, 1 cmH2O at 4 Hz, the induced airflow at 4 Hz is measured, the conductance of the airway calculated by dividing the amplitude of the induced airflow by the pressure modulation amplitude, and the additional requirement imposed that the treatment pressure is only increased if said conductance is greater than a threshold.

Closed airway apneas are most likely to occur at low CPAP pressures, because high CPAP pressures splint the airway partially or completely open, whereas pressure-induced open airway apneas are most likely to occur at high CPAP pressures, at least partially because high CPAP pressures increase lung volume and thereby stimulate the Hering-Breuer reflex, leading to inhibition of breathing. Therefore, the lower the existing CPAP pressure, the more likely an apnea is to be of the closed airway variety, and the more appropriate it is to increase the treatment pressure, whereas the higher the existing CPAP pressure, the more likely an apnea is to be of the open airway variety, and the more appropriate it is to leave the CPAP pressure unchanged. Generally apneas of less than 10 seconds duration are regarded as non-pathological, and there is no need to increase CPAP pressure, whereas very long apneas require treatment. The present invention will correctly increase the CPAP pressure for most closed airway apneas, and correctly leave the CPAP pressure unchanged for most open airway apneas.

The present invention can be combined with an independent pressure increase in response to indicators of partial upper airway obstruction such as snoring or changes in shape of the inspiratory flow-time curve. In this way it is possible in most subjects to achieve pre-emptive control of the upper airway, with pressure increases in response to partial upper airway obstruction preventing the occurrence of closed airway apneas. In the minority of subjects in whom pre-emptive control is not achieved, this combination will also correctly increase the CPAP pressure in response to those closed airway apneas that occur at low CPAP pressure without prior snoring or changes in the shape of the inspiratory flow-time curve. Furthermore, the combination will avoid falsely increasing the CPAP pressure in response to open airway apneas induced by high pressure.

Some open airway apneas can occur at low pressure. By combining the forced oscillation method with the present invention, with the additional requirement that there be no increase in pressure if the forced oscillation method detects an open airway, false increases in pressure in response to open airway apneas at low pressure will be largely avoided.

BRIEF DESCRIPTION OF THE DRAWINGS

Embodiments of the invention will now be described with reference to the accompanying drawings, in which.

DETAILED DESCRIPTION OF PREFERRED EMBODIMENTS

Figure 1:
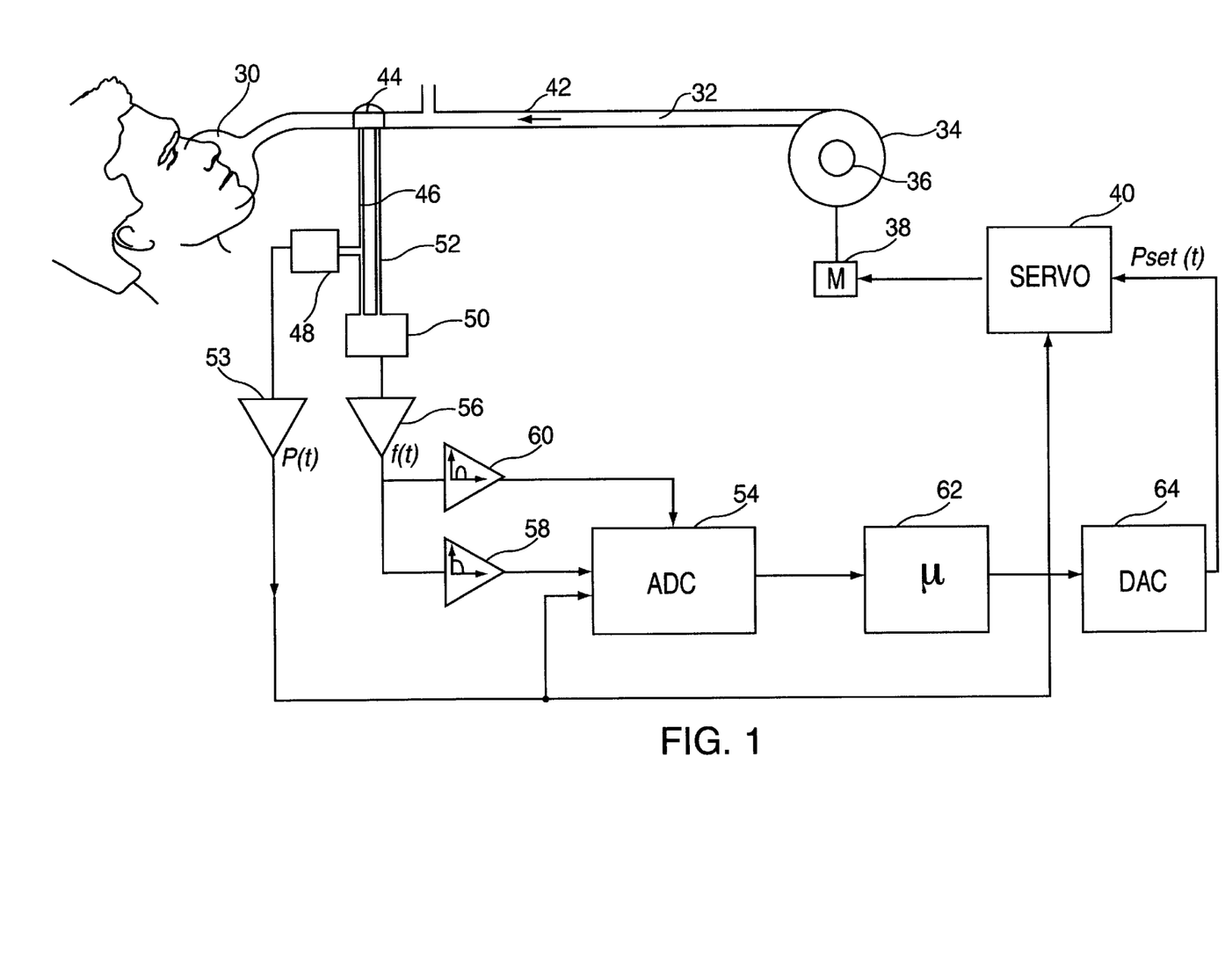
FIG. 1 shows, in diagrammatic form, apparatus embodying the invention.

FIG. 1 shows, in diagrammatic form, CPAP apparatus in accordance with one embodiment. A mask 30, whether either a nose mask and/or a face mask, is sealingly fitted to a patient's face. Breathable gas in the form of fresh air, or oxygen enriched air, enters the mask 30 by flexible tubing 32 which, in turn, is connected with a motor driven turbine blower 34 to which there is provided an air inlet 36. The motor 38 for the turbine is controlled by a motor-servo unit 40 to commence, increase or decrease the pressure of air supplied to the mask 30 as CPAP treatment. The mask 30 also includes an exhaust port 42 that is close to the junction of the tubing 32 with the mask 30.

Interposed between the mask 30 and the exhaust 42 is a linear flow-resistive element 44. In practice, the distance between mask 30 and exhaust 42, including flow resistive element 44 is very short so as to minimize deadspace volume. The mask side of the flow-resistive element 44 is connected by a first small bore tube 46 to a mask pressure transducer 48 and to an input of a differential pressure transducer 50. Pressure at the other side of the flow-resistive element 44 is conveyed to the other input of the differential pressure transducer 50 by a second small bore tube 52.

The mask pressure transducer 48 generates an electrical signal in proportion to the mask pressure, which is amplified by a first amplifier 53 and passed both to a multiplexer/ADC unit 54 and to the motor-servo unit 40. The function of the signal provided to the motor-servo unit 40 is as a form of feedback to ensure that the actual mask static pressure is controlled to be closely approximate to the set point pressure.

The differential pressure sensed across the linear flow-resistive element 44 is output as an electrical signal from the differential pressure transducer 50, and amplified by a second amplifier 56. The output signal from the second amplifier 56 therefore represents a measure of the mask airflow. The linear flow-resistive element 44 can be constructed using a flexible-vaned iris. Alternatively, a fixed orifice can be used, in which case a linearization circuit is included in the first amplifier 53, or a linearization step such as table lookup included in the operation of controller 62.

The output signal from the amplifier 56 is low-pass filtered by the low-pass filter 58, typically with an upper limit of 10 Hz, in order to remove non-respiratory noise. The second amplifier 56 output signal is also bandpassed by the bandpass filter 60, and typically in a range of 30–100 Hz to yield a snoring signal. The outputs from both the low-pass filter 58 and the bandpass filter 60 are provided to the digitizer or ADC unit 54. The digitized, respiratory airflow, snore, and mask pressure signals from ADC unit 54 are passed to a controller 62, typically constituted by a microprocessor based device also provided with program memory and data processing storage memory.

The controller 62 outputs a pressure request signal which is converted to a voltage by a DAC unit 64, and passed to the motor-servo unit 40. This signal therefore represents the set point pressure $P_{set}(t)$ to be supplied by the turbine or blower 34 to the mask 30 in the administration of CPAP treatment. The controller 62 is programmed to perform a number of processing functions, as presently will be described.

As an alternative to the mask pressure transducer 48, a direct pressure/electrical solid state transducer (not shown) can be mounted from the mask with access to the space therewithin, or to the air delivery tubing 32 proximate the point of entry to the mask 30.

Figure 2:
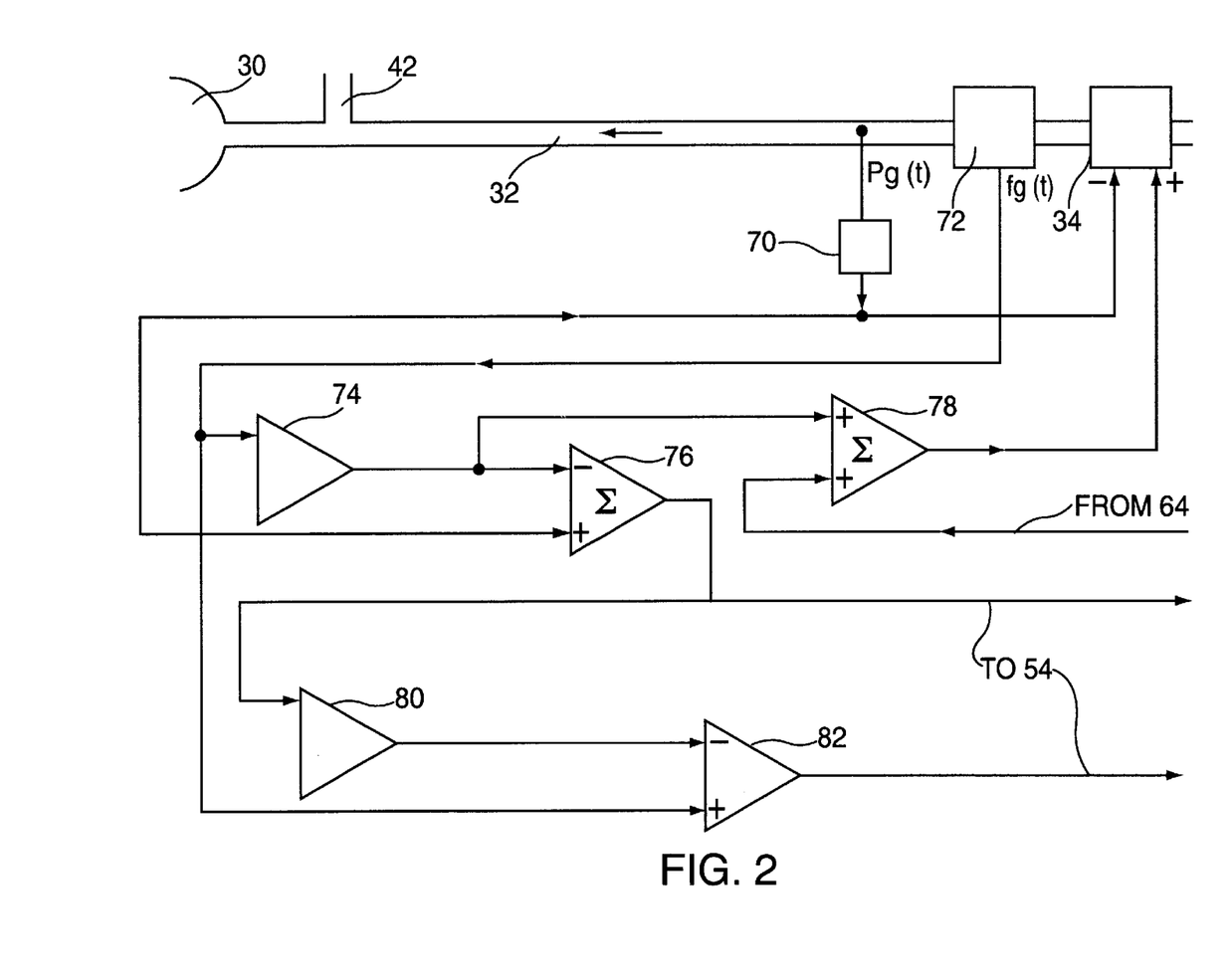
FIG. 2 shows an alternative arrangement of the apparatus of FIG. 1.

Further, it may not be convenient to mount the linear flow-resistive element 44 at or near the mask 30, nor to measure the mask pressure at or near the mask. An alternative arrangement, where the flow and pressure transducers are mounted at or near the air pressure generator (in the embodiment being the turbine or blower 34) is shown in FIG. 2.

The pressure $p_g(t)$ occurring at the pressure generator outlet is measured by a pressure transducer 70. The flow $f_g(t)$ through tubing 32 is measured with flow sensor 72 provided at the output of the turbine or blower 34. The pressure loss along tubing 32 is calculated in pressure loss calculation element 74 from the flow through the tube $f_g(t)$, and a knowledge of the pressure-flow characteristic of the tubing, for example by table lookup. The pressure at the mask $p_m$ is then calculated in first subtraction element 76 by subtracting the tube pressure loss from $p_g(t)$.

The pressure loss along tube 32 is then added to the desired set pressure at the mask $p_{set}(t)$ in summation element 78 to yield the desired instantaneous pressure at the pressure generator. Preferably, the controller of the pressure generator has a negative feedback input from the pressure transducer 70, so that the desired pressure from summation element 78 is achieved more accurately. The flow through the exhaust 42 is calculated from the pressure at the mask (calculated in first subtraction element 76) from the pressure-flow characteristic of the exhaust in exhaust flow calculation element 80, for example by table lookup. Finally, the mask flow is calculated by subtracting the flow through the exhaust 42 from the flow through the tubing 32, in second subtraction element 82.

The methodology put into place by the controller 62 will now be described. In a first embodiment, there is a pressure response to apneas, but not to indicators of partial obstruction, and therefore snore detection bandpass filter 60 is not required. The controller implements the following pseudo-code.

Set apnea duration to zero
Clear "start of breath" flag
Set initial CPAP pressure to 4 cmH2O.
Set maximum delta pressure due to apnea to 6 cmH2O.
Set top roll-off pressure to initial CPAP pressure plus maximum delta pressure due to apnea.
REPEAT
   Sample mask airflow (in L/sec) at 50 Hz.
   Calculate mask leak as mask airflow low pass filtered with a time constant of 10 seconds.
   Check for presence and duration of any apnea.
   Check for start of breath.
   IF start of breath flag set:
      IF apnea duration greater than 10 seconds AND current CPAP pressure less than top roll-off pressure:
         Set delta pressure for this apnea to (top roll-off pressure—current CPAP pressure)/maximum delta pressure due to apnea times 8 cmH2O per minute of apnea duration.
         Add delta pressure for this apnea to total delta pressure due to apnea, and truncate to maximum delta pressure due to apnea.
         Reset apnea duration to zero.
      ELSE
         Reduce total delta pressure due to apnea with a time constant of 20 minutes.
      END
      Set CPAP pressure to initial CPAP pressure plus total delta pressure due to apnea.
      Clear start of breath flag.
   END
END This implementation is suitable for subjects in whom obstructive apneas are controlled at a CPAP pressure of less than 10 cmH2O. Increasing the maximum delta pressure due to apnea from 6 cmH2O to 10 cmH2O would permit the prevention of obstructive apneas in the majority of subjects, in exchange for an increase in undesirable pressure increases due to open airway apneas.

Figure 4:
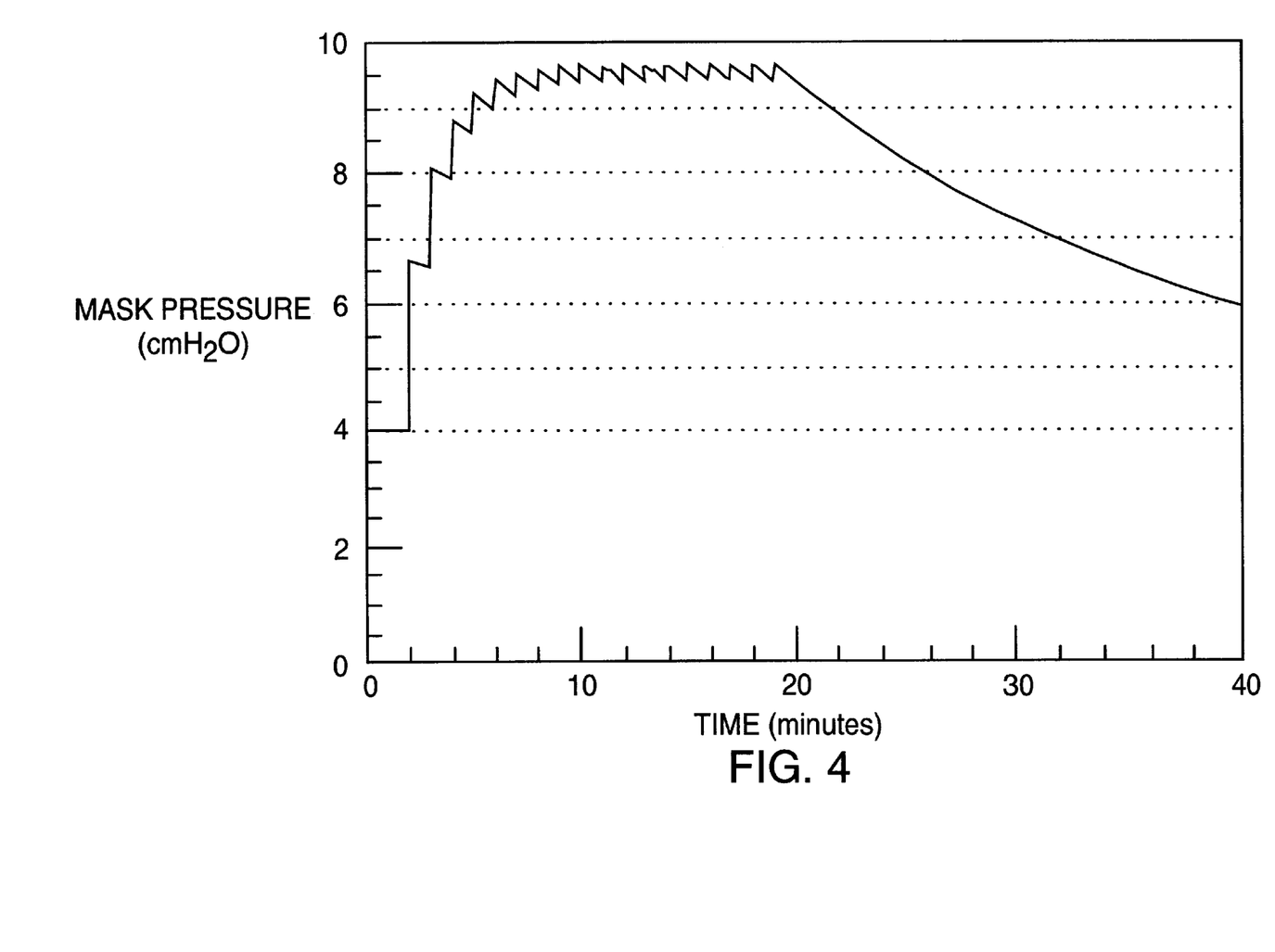
FIG. 4 shows a graph of CPAP treatment pressure versus time for a preferred embodiment of the invention, tested on a breathing simulator in which there are repetitive 20 second apneas every 60 seconds from the second to the twentieth minute, and no further apneas thereafter.

The procedure "Check for presence and duration of any apnea" can be implemented using the following pseudocode:
   Calculate 2 second RMS airflow as the RMS airflow over the previous 2 seconds.
   Calculate longterm average RMS airflow as the 2 second RMS airflow, low pass filtered with a time constant of 300 seconds.
   IF 2 second RMS airflow is less than 25% of longterm average RMS airflow:
   Mark apnea detected and increment apnea duration by 1/50 second.
   END The procedure, "Check for start of breath" is implemented by the following pseudocode:
   IF respiratory airflow is inspiratory AND respiratory airflow on previous sample was not inspiratory:
   Set "start of breath" flag.
   END FIG. 4 shows the above method and apparatus in operation. The mask 30 was connected to a piston driven breathing simulator set to a normal respiratory rate and depth, and programmed to introduce a 20 second apnea once per minute from the 2nd minute to the 20th minute. In operation, the pressure remained at the initial pressure of 4 cmH2O until the first apnea, which led to a brisk increase in mask pressure. The pressure then decayed slightly during the subsequent 40 seconds of normal breathing. Subsequent apneas produced smaller increments, and the mask pressure settled out to approximately 9.5 cmH2O. In most actual patients, the number of apneas would reduce as the pressure increased. Because the pressure due to repetitive apneas cannot exceed 10 cmH2O, and most pressure-induced open airway apneas occur at very high pressures typically above 10 cmH2O, this algorithm will not falsely or needlessly increase pressure in response to most pressure-induced open airway apneas, thus avoiding a vicious cycle of high pressure leading to open airway apneas leading to yet further pressure increase.

The above embodiment can be considerably improved by the addition of independent pressure increases in response to partial upper airway obstruction indicated, by the presence of snoring or changes in the shape of the inspiratory flow-vs-time curve. In the majority of subjects, in whom substantial periods of snoring or flow limitation exist prior to any closed airway apneas, the CPAP pressure will increase in response to said snoring and/or changes in the shape of the inspiratory flow-vs-time curve, to a sufficient level to largely eliminate severe partial obstruction, without any apneas of any kind occurring. In those subjects in whom closed airway apneas appear with little or no prior period of partial obstruction, the first few apneas will produce a brisk increase in CPAP pressure as previously discussed, and in general this will provide sufficient partial support to the airway to permit periods of detectable partial obstruction, preventing any further apneas from occurring.

This second embodiment is implemented using the following pseudocode.

Set initial CPAP pressure to 4 cmH2O.
Set apnea duration to zero
Clear "start of breath" flag
REPEAT every 1/50 of a second
  Sample mask pressure (in cmH2O), mask airflow (in L/sec), and snore (1 unit corresponds loosely to a typical snore).
  Calculate mask leak as mask airflow low pass filtered with a time constant of 10 seconds.
  Adjust snore signal for machine noise.
  Check for presence and duration of any apnea.
  Check for start of breath.
  IF start of breath flag set:
    IF apnea duration greater than 10 seconds AND current CPAP pressure less than 10 cmH2O:
      Set delta pressure for this apnea to (10−current CPAP pressure)/6 times 8 cmH2O per minute of apnea duration.
      Add delta pressure for this apnea to total delta pressure due to apnea, and truncate to 16 cmH2O
      Reset apnea duration to zero.
    ELSE
      Reduce total delta pressure due to apnea with a time constant of 20 minutes.
    END
    Calculate flow limitation index.
    Calculate flow limitation threshold.
    IF flow limitation index is less than said threshold:
      Set flow limitation delta pressure for this breath to 3 cmH2O times (threshold-flow limitation index).
      Add flow limitation delta pressure for this breath to total delta pressure due to flow limitation, and truncate to 16 cmH2O.
    ELSE
      Reduce total delta pressure due to flow limitation with a time constant of 10 minutes.
    END
    Calculate mean snore for breath.
    Calculate snore threshold.
    IF mean snore exceeds said threshold:
      set delta pressure due to snore for this breath to 3 cmH2O times (mean snore for this breath−threshold).
      Add delta pressure due to snore for this breath to total delta pressure due to snore, and truncate to 16 cmH2O.
    ELSE
      Reduce total delta pressure due to snore with a time constant of 10 minutes.
    END
    Set CPAP pressure to 4 cmH2O plus total delta pressure due to apnea plus total delta pressure due to snore plus total delta pressure due to flow limitation, and truncate to 20 cmH2O.
    Clear start of breath flag.
  END
END In the above implementation, apneas can only cause the CPAP pressure to rise as far as 10 cmH2O, but subsequently, indicators of partial obstruction can increase the CPAP pressure to 20 cmH2O, which is sufficient to treat the vast majority of subjects.

The procedure "Adjust snore for machine noise" is described by the following pseudocode:

Machine noise=$K1$*mask pressure+$K2$*mask pressure squared+$K3$*mask flow+$K4$*time derivative of mask flow+$K5$*time derivative of mask pressure.

Adjusted snore signal=raw snore signal−machine noise.

where the constants $K1$ to $K5$ are determined empirically for any particular physical embodiment, and for a particular machine may be zero. In other embodiments, blower fan speed measured with a tachometer or pressure at the blower may be used instead of mask pressure.

The procedure "Calculate flow limitation index" is described by the following pseudocode:

Identify the inspiratory portion of the preceding breath
Note the duration of inspiration.
Calculate the mean inspiratory airflow.
For each sample point over said inspiratory portion, calculate a normalized inspiratory airflow by dividing the inspiratory airflow by the mean inspiratory airflow.
Identify a mid-portion consisting of those sample points between 25% and 75% of the duration of inspiration.
Calculate the flow limitation index as the RMS deviation over said mid-portion of (normalized inspiratory airflow−1)

Figure 3:
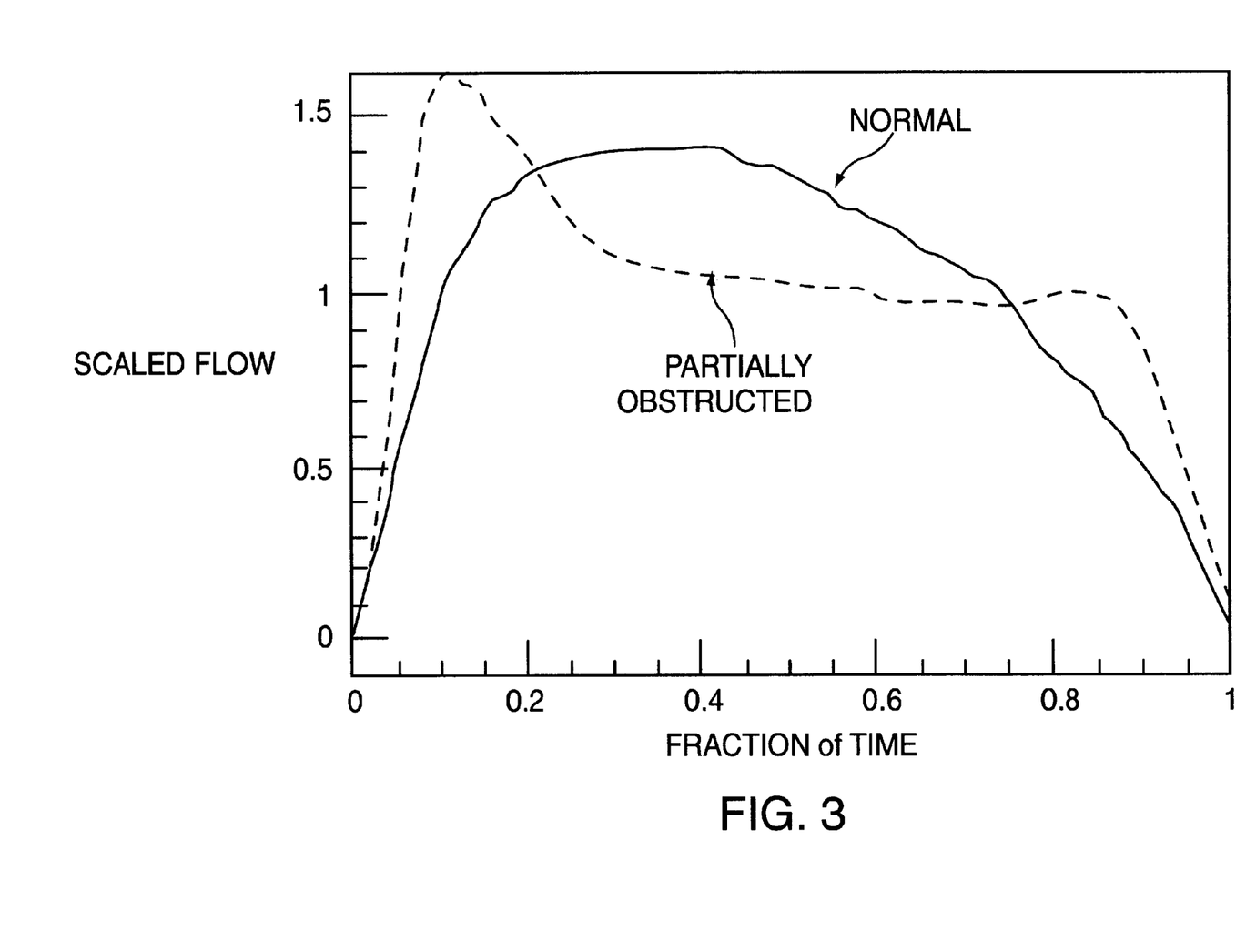
FIG. 3 shows a graph of scaled (normalized) air flow with time for normal and partially obstructed inspiration.

The logic of the above algorithm is as follows: partial upper airway obstruction in untreated or partially treated Obstructive Sleep Apnea syndrome, and the related Upper Airway Resistance syndrome, leads to mid-inspiratory flow limitation, as shown in FIG. 3, which shows typical inspiratory waveforms respectively for normal and partially obstructed breaths, after scaling (normalizing) to equal mean amplitude and duration.

For a totally flow-limited breath, the flow amplitude vs. time curve would be a square wave and the RMS deviation would be zero. For a normal breath, the RMS deviation is approximately 0.2 units, and this deviation decreases as the flow limitation becomes more severe.

In some patients, it is not possible to prevent all upper airway obstruction, even at maximum pressure. In addition, there is a trade-off between the possible advantage of increasing the pressure in response to snoring and the disadvantage of increased side effects. This trade-off is implemented in procedure "calculate snore threshold" by looking up the snore threshold in the following table:

| Pressure (cm H$_2$O) | Threshold (snore units) | Description |
|---|---|---|
| <10 | 0.2 | very soft |
| 10–12 | 0.25 | |
| 12–14 | 0.3 | soft |
| 14–16 | 0.4 | |
| 16–18 | 0.6 | moderate |
| >18 | 1.8 | loud |

For similar reasons, the procedure "calculate flow limitation threshold" sets the flow limitation threshold to a lower value corresponding to more severe flow limitation, if the pressure is already high or if there is a large leak:

IF mask leak is greater than 0.7 L/sec
        set leak roll-off to 0.0
    ELSE if mask leak is less than 0.3 L/sec
        set leak roll-off to 1.0
    ELSE
        set leak roll-off to (0.7-mask leak)/0.4
    END
    Set pressure roll-off to (20-mask pressure)/16
    Set flow limitation threshold to 0.15 times pressure roll-off times leak roll-off Some subjects will have occasional open airway apneas at sleep onset during stage 1 sleep and therefore at low pressure, and the above algorithm will incorrectly increase CPAP pressure in response to these events. However, such apneas are not usually repetitive, because the subject quickly becomes more deeply asleep where such events do not occur, and furthermore, the false pressure increments become smaller with repeated events. Once the subject reaches deeper sleep, any such falsely increased pressure will diminish. However, it is still advantageous to avoid falsely or needlessly increasing pressure in response to such sleep onset open airway apneas.

As previously discussed, one prior art method for avoiding unnecessary increases in pressure in response to open airway apneas is to determine the conductance of the airway during an apnea using the forced oscillation method, and only increase mask pressure if the conductance is less than a threshold. However, if the nasal airway is narrow or if the subject has lung disease, the airway conductance may be low even in the presence of an open airway and the forced oscillation method may still falsely increase pressure in response to open airway apneas. Conversely, the combination of the forced oscillation method with the present invention has the added advantage that in most cases open airway apneas are correctly detected by the forced oscillation method, but in those cases where the forced oscillation method falsely reports a closed airway, the mask pressure will not increase above 10 cmH2O, thus preventing runaway increases in pressure. This is demonstrated in a third embodiment using the following pseudo-code:

Set apnea duration to zero
    Clear "start of breath" flag
    REPEAT every 1/50 of a second
        Sample mask pressure (in cmH2O), mask airflow (in L/sec), and snore (1 unit corresponds loosely to a typical snore).
        Calculate mask leak as mask airflow low pass filtered with a time constant of 10 seconds.
        Adjust snore signal for machine noise.
        Check for presence and duration of any apnea.
        IF apnea in progress:
            measure conductance of airway using forced oscillation method.
        END
        Check for start of breath.
        IF start of breath flag set:
            IF apnea duration greater than 10 seconds AND current CPAP pressure less than 10 cmH2O AND airway conductance measured using forced oscillation method is less than 0.05 cmH2O/L/sec:
                Set delta pressure for this apnea to (10−current CPAP pressure)/6 times 8 cmH2O per minute of apnea duration.
                Add delta pressure for this apnea to total delta pressure due to apnea, and truncate to 16 cmH2O
                Reset apnea duration to zero.
            ELSE
                Reduce total delta pressure due to apnea with a time constant of 20 minutes.
            END
            Calculate flow limitation index.
            Calculate flow limitation threshold.
            IF flow limitation index is less than said threshold:
                Set flow limitation delta pressure for this breath to 3 cmH2O times (threshold-flow limitation index).
                Add flow limitation delta pressure for this breath to total delta pressure due to flow limitation, and truncate to 16 cmH2O.
            ELSE
                Reduce total delta pressure due to flow limitation with a time constant of 10 minutes.
            END
            Calculate mean snore for breath.
            Calculate snore threshold.
            IF mean snore exceeds said threshold:
                set delta pressure due to snore for this breath to 3 cmH2O times (mean snore for this breath−threshold).
                Add delta pressure due to snore for this breath to total delta pressure due to snore, and truncate to 16 cmH2O.
            ELSE
                Reduce total delta pressure due to snore with a time constant of 10 minutes.
            END
            Set CPAP pressure to 4 cmH2O plus total delta pressure due to apnea plus total delta pressure due to snore plus total delta pressure due to flow limitation, and truncate to 20 cmH2O.
            Clear start of breath flag.
        END
    END The procedure, "measure airway conductance using the forced oscillation method" can be implemented using the following pseudocode:

Modulate airway pressure with an amplitude of 1 cmH2O peak to peak at 4 Hz.
    Measure amplitude of airflow signal at 4 Hz.
    Measure component of mask pressure signal at 4 Hz.
    Set conductance equal to said airflow amplitude divided by said mask pressure amplitude.

More complex variants of CPAP therapy, such as bi-level CPAP therapy or therapy in which the mask pressure is modulated within a breath, can also be monitored and/or controlled using the methods described herein.

Numerous alterations and modification, as would be apparent to one skilled in the art, can be made without departing from the basic inventive concept.

We claim:

1. A method for the administration of CPAP therapy comprising the steps of:
   supplying breathable gas to a patient's airway at a treatment pressure;
   determining a measure of respiratory airflow;
   determining the onset of an apnea from a reduction in the measure of respiratory airflow below a threshold and, in response to the onset of an apnea, increasing the treatment pressure by an amount which is a decreasing function of the treatment pressure immediately before the apnea onset; and
   decreasing the pressure following a time interval during which there was no apnea.

2. A method for the administration of CPAP therapy comprising the steps of:
   supplying breathable gas to a patient's airway at a treatment pressure;
   determining a measure of respiratory airflow;
   determining the occurrence of an apnea from a reduction in the measure of respiratory airflow below a threshold and, in response to the presence of an apnea, (i) determining the duration of the apnea, and (ii) increasing the treatment pressure by an amount which is an increasing function of the duration of the apnea; and
   decreasing the pressure following a time interval during which there was no apnea.

3. A method for the administration of CPAP therapy comprising the steps of:
   supplying breathable gas to a patient's airway at a treatment pressure;
   determining a measure of respiratory airflow;
   determining the occurrence of an apnea from a reduction in the measure of respiratory airflow below a threshold and, in response to the presence of an apnea, (i) determining the duration of the apnea; and (ii) increasing the treatment pressure by an amount which is an increasing function of the duration of the apnea and a decreasing function of the treatment pressure immediately before the apnea; and
   decreasing the pressure following a time interval ring which there was no apnea.

4. A method as claimed in claim 1, 2 or 3 wherein the increase in treatment pressure is zero if the treatment pressure before the apnea exceeded a pressure threshold.

5. A method as claimed in claim 4 wherein the increase in pressure below the pressure threshold is an increasing function of the duration of the apnea, multiplied by the difference between the pressure threshold and the current treatment pressure.

6. A method as claimed in claim 5 wherein said increasing function of apnea duration is a linear function of apnea duration.

7. A method as claimed in claim 4 wherein the pressure threshold is 10 cmH$_2$O.

8. A method as claimed in claim 1, 2 or 3 wherein the occurrence of an apnea is determined by the steps of:
   calculating the RMS respiratory airflow over a short time interval;
   calculating the RMS respiratory airflow over a longer time interval; and
   determining the onset of an apnea if the RMS respiratory airflow over said short time interval is less than a predetermined fraction of the RMS respiratory airflow over said longer time interval.

9. A method as claimed in claim 1, 2 or 3 wherein in the continued absence of apneas the treatment pressure is gradually reduced towards an initial treatment pressure.

10. A method as claimed in claim 1, 2 or 3 comprising the further steps of:
    in the absence of an apnea, determining the presence of a partial obstruction; and if a partial obstruction is present, increasing the treatment pressure.

11. A method as claimed in claim 9 wherein the presence of a partial obstruction is determined from either (a) the shape of the patient's inspiratory flow vs time curve, or (b) the presence of snoring, or (c) both.

12. A method as claimed in claim 1, 2 or 3 comprising the further steps of:
    if an apnea is occurring, determining whether the patient's airway is patent during the apnea; and
    if the airway is patent, not increasing the treatment pressure.

13. A method as claimed in claim 12 wherein the patency of the airway is determined by the steps of:
    modulating the treatment pressure at a known frequency;
    measuring the component of the respiratory airflow at the modulation frequency;
    calculating the conductance of the airway as the ratio of the amplitude of said component of the respiratory airflow to the amplitude of the mask pressure modulation; and
    determining that the airway is patent if the conductance exceeds a conductance threshold.

14. CPAP treatment apparatus comprising:
    a controllable flow generator operable to provide breathable gas at a pressure elevated above atmospheric;
    a gas delivery tube coupled to said flow generator;
    a patient mask coupled to said gas delivery tube to receive breathable gas from said flow generator and to provide said gas, at a desired treatment pressure, to a patient's airway;
    a controller operable to receive an input signal and to control the magnitude of the treatment pressure provided by said flow generator; and
    sensor means to sense patient respiratory airflow and to generate an input signal to said controller;
    said controller being programmed to determine the onset of an apnea from a reduction in said respiratory airflow below a threshold, in response to the onset of an apnea to cause said flow generator to increase the treatment pressure by an amount which is a decreasing function of the treatment pressure immediately prior to said apnea, and to decrease the pressure following a time interval during which there was no apnea.

15. CPAP treatment apparatus comprising:
    a controllable flow generator operable to provide breathable gas at a pressure elevated above atmospheric;
    a gas delivery tube coupled to said flow generator;
    a patient mask coupled to said gas delivery tube to receive breathable gas from said flow generator and to provide said gas, at a desired treatment pressure, to a patient's airway;
    a controller operable to receive an input signal and to control the magnitude of the treatment pressure provided by said flow generator; and
    sensor means to sense patient respiratory airflow and to generate a signal input to said controller;

said controller being programmed to determine the occurrence of an apnea from a reduction in said respiratory airflow below a threshold, in response to the presence of an apnea to determine the duration of said apnea and to cause said flow generator to increase the treatment pressure by an amount which is an increasing function of said apnea duration, and to decrease the pressure following a time interval during which there was no apnea.

16. CPAP treatment apparatus comprising:

a controllable flow generator operable to provide breathable gas at a pressure elevated above atmospheric;

a gas delivery tube coupled to said flow generator;

a patient mask coupled to said gas delivery tube to receive breathable gas from said flow generator and to provide said gas, at a desired treatment pressure, to a patient's airway;

a controller operable to receive an input signal and to control the magnitude of the treatment pressure provided by said flow generator; and sensor means to sense patient respiratory airflow and to generate a signal input to said controller;

said controller being programmed to determine the occurrence of an apnea from a reduction in said respiratory airflow below a threshold, in response to the presence of an apnea to determine the duration of said apnea and to cause said flow generator to increase the treatment pressure by an amount which is an increasing function of said apnea duration and a decreasing function of the treatment pressure immediately prior to said apnea, and to decrease the pressure following a time interval during which there was no apnea.

17. Apparatus as claimed in claim 14, 25 or 26 wherein the increase in treatment pressure is zero if the treatment pressure before the apnea exceeded a pressure threshold.

18. Apparatus as claimed in claim 17 wherein the increase in pressure below the pressure threshold is an increasing function of the duration of the apnea, multiplied by the difference between the pressure threshold and the current treatment pressure.

19. Apparatus as claimed in claim 18 wherein said increasing function of apnea duration is a linear function of apnea duration.

20. Apparatus as claimed in claim 17 wherein the pressure threshold is 10 cmH$_2$O.

21. Apparatus as claimed in claim 14, 15 or 16 wherein said controller determines the occurrence of an apnea by:

calculating the RMS respiratory airflow over a short time interval;

calculating the RMS respiratory airflow over a longer time interval; and determining the onset of an apnea if the RMS respiratory airflow over said short time interval is less than a predetermined fraction of the RMS respiratory airflow over said longer time interval.

22. Apparatus as claimed in claim 14, 15 or 16 wherein said controller is further operable to cause a gradual reduction in the treatment pressure towards an initial treatment pressure in the absence of an apnea.

23. Apparatus as claimed in claim 14, 15 or 16 wherein said controller is further operable, in the absence of an apnea, to determine the presence of a partial obstruction; and if a partial obstruction is present, to increase the treatment pressure.

24. Apparatus as claimed in claim 23 wherein the presence of a partial obstruction is determined from either (a) the shape of the patient's inspiratory flow vs time curve, or (b) the presence of snoring, or (c) both.

25. Apparatus as claimed in claim 14, 15 or 16 wherein said controller is operable, if an apnea is occurring, to determine whether the patient's airway is patent during the apnea; and, if the airway is patent, to set the increase in treatment pressure to zero.

26. Apparatus as claimed in claim 25 wherein said controller determines the patency of the airway by:

modulating the treatment pressure at a known frequency;

measuring the component of the respiratory airflow at the modulation frequency;

calculating the conductance of the airway as the ratio of the amplitude of said component of the respiratory airflow to the amplitude of the mask pressure modulation; and determining that the airway is patent if the conductance exceeds a conductance threshold.

27. CPAP treatment apparatus comprising:

a controllable source of breathable gas to be provided to a patient at a treatment pressure elevated above atmospheric; and a controller operable to receive input signals representing patient respiratory airflow, and to control the magnitude of the treatment pressure provided by said source of breathable gas; said controller being programmed to determine the onset of an apnea from a reduction in said respiratory airflow below a threshold, in response to the onset of an apnea to cause said flow generator to increase the treatment pressure by an amount which is a decreasing function of the treatment pressure immediately prior to said apnea, and to decrease the pressure following a time interval during which there was no apnea.

28. CPAP treatment apparatus comprising:

a controllable source of breathable gas to be provided to a patient at a treatment pressure elevated above atmospheric; and a controller operable to receive input signals representing patient respiratory airflow, and to control the magnitude of the treatment pressure provided by said source of breathable gas; said controller being programmed to determine the occurrence of an apnea from a reduction in said respiratory airflow below a threshold, in response to the presence of an apnea to determine the duration of said apnea and to cause said flow generator to increase the treatment pressure by an amount which is an increasing function of said apnea duration, and to decrease the pressure following a time interval during which there was no apnea.

29. CPAP treatment apparatus comprising:

a controllable source of breathable gas to be provided to a patient at a treatment pressure elevated above atmospheric; and a controller operable to receive input signals representing patient respiratory airflow, and to control the magnitude of the treatment pressure provided by said source of breathable gas; said controller being programmed to determine the occurrence of an apnea from a reduction in said respiratory airflow below a threshold, in response to the presence of an apnea to determine the duration of said apnea and to cause said flow generator to increase the treatment pressure by an amount which is an increasing function of said apnea duration and a decreasing function of the treatment pressure immediately prior to said apnea, and to decrease the pressure following a time interval during which there was no apnea.

30. Apparatus as claimed in claim 27, 28 or 29 wherein the increase in treatment pressure is zero if the treatment pressure before the apnea exceeded a pressure threshold.

31. Apparatus as claimed in claim 30 wherein the increase in pressure below the pressure threshold is an increasing function of the duration of the apnea, multiplied by the difference between the pressure threshold and the current treatment pressure.

32. Apparatus as claimed in claim 31 wherein said increasing function of apnea duration is a linear function of apnea duration.

33. Apparatus as claimed in claim 31 wherein said increasing function of apnea duration is zero for zero apnea duration, and exponentially approaches an upper limit as apnea duration increases indefinitely.

34. Apparatus as claimed in claim 30 wherein the pressure threshold is 10 cmH$_2$O.

35. Apparatus as claimed in claim 27, 28 or 29 wherein said controller determines the occurrence of an apnea by:
   calculating the RMS respiratory airflow over a short time interval;
   calculating the RMS respiratory airflow over a longer time interval; and
   determining the onset of an apnea if the RMS respiratory airflow over said short time interval is less than a predetermined fraction of the RMS respiratory airflow over said longer time interval.

36. Apparatus as claimed in claim 27, 28 or 29 wherein in the continued absence of apneas the treatment pressure is gradually reduced towards an initial treatment pressure.

37. Apparatus as claimed in claim 27, 28 or 29 wherein said controller is further operable, in the absence of an apnea, to determine the presence of a partial obstruction; and if a partial obstruction is present, to increase the treatment pressure.

38. Apparatus as claimed in claim 37 wherein the presence of a partial obstruction is determined from either (a) the shape of the patient's inspiratory flow vs time curve, or (b) the presence of snoring, or (c) both.

39. Apparatus as claimed in claim 27, 28 or 29 wherein said controller is operable, if an apnea is occurring, to determine whether the patient's airway is patent during the apnea; and, if the airway is patent, to set the increase in treatment pressure to zero.

40. Apparatus as claimed in claim 37 wherein said controller determines the patency of the airway by:
   modulating the treatment pressure at a known frequency;
   measuring the component of the respiratory airflow at said modulation frequency; calculating the conductance of the airway as the ratio of the amplitude of said component of the respiratory airflow to the amplitude of the mask pressure modulation; and
   determining that the airway is patent if the conductance exceeds a conductance threshold.

* * * * *